(12) United States Patent
Shah et al.

(10) Patent No.: US 8,808,654 B2
(45) Date of Patent: Aug. 19, 2014

(54) PROCESS FOR SULFUR REMOVAL FROM REFINERY OFF GAS

(75) Inventors: Minish Mahendra Shah, East Amherst, NY (US); Raymond Francis Drnevich, Clarence Center, NY (US); Vasilis Papavassiliou, Williamsville, NY (US)

(73) Assignee: Praxair Technology, Inc., Danbury, CT (US)

( * ) Notice: Subject to any disclaimer, the term of this patent is extended or adjusted under 35 U.S.C. 154(b) by 853 days.

(21) Appl. No.: 12/856,705

(22) Filed: Aug. 16, 2010

(65) Prior Publication Data

US 2011/0077437 A1    Mar. 31, 2011

Related U.S. Application Data

(60) Provisional application No. 61/246,592, filed on Sep. 29, 2009.

(51) Int. Cl.

| | |
|---|---|
| *C10G 70/00* | (2006.01) |
| *C10G 70/02* | (2006.01) |
| *C10G 70/06* | (2006.01) |
| *B01D 53/48* | (2006.01) |
| *B01D 53/86* | (2006.01) |

(52) U.S. Cl.
CPC ............... *B01D 53/48* (2013.01); *C10G 70/00* (2013.01); *C10G 70/02* (2013.01); *C10G 70/06* (2013.01); *B01D 2257/306* (2013.01); *C10G 2300/202* (2013.01); *B01D 53/869* (2013.01); *C10G 2300/207* (2013.01); *B01D 2256/24* (2013.01); *B01D 53/8603* (2013.01)
USPC ................ 423/228; 95/149; 95/235; 423/224

(58) Field of Classification Search
USPC .............................. 95/149, 235; 423/224, 228
See application file for complete search history.

(56) References Cited

U.S. PATENT DOCUMENTS

| | | | |
|---|---|---|---|
| 4,865,820 A | 9/1989 | Dunster et al. | |
| 5,110,563 A | 5/1992 | Noakes et al. | |
| 5,401,391 A | 3/1995 | Collins et al. | |
| 5,522,723 A | 6/1996 | Durst et al. | |
| 5,886,056 A | 3/1999 | Hershkowitz et al. | |
| 6,267,912 B1 | 7/2001 | Hershkowitz et al. | |
| 6,335,474 B1 | 1/2002 | Ostberg et al. | |
| 6,447,745 B1 | 9/2002 | Feeley et al. | |
| 6,471,937 B1 | 10/2002 | Anderson et al. | |
| 6,787,115 B2 | 9/2004 | Goebel | |
| 6,981,994 B2 | 1/2006 | Drnevich et al. | |
| 7,037,485 B1 * | 5/2006 | Drnevich et al. | ............. 423/652 |
| 7,041,271 B2 | 5/2006 | Drnevich et al. | |
| 7,255,840 B2 | 8/2007 | Papavassiliou et al. | |
| 7,261,750 B1 | 8/2007 | Antenrieth et al. | |
| 7,395,670 B1 | 7/2008 | Drnevich et al. | |
| 7,427,388 B2 | 9/2008 | Garg et al. | |
| 7,521,139 B2 | 4/2009 | Foger | |
| 7,547,422 B2 | 6/2009 | Papavassiliou et al. | |
| 2004/0096391 A1 | 5/2004 | Franz et al. | |
| 2005/0074642 A1 | 4/2005 | Foger | |
| 2005/0095185 A1 | 5/2005 | Gary | |
| 2005/0207970 A1 | 9/2005 | Garg et al. | |
| 2009/0013600 A1 | 1/2009 | Drnevich et al. | |
| 2009/0050534 A1 | 2/2009 | Ripperger | |

FOREIGN PATENT DOCUMENTS

EP    0486174 A1    5/1992

OTHER PUBLICATIONS

Freni, S. et al., "Hydrogen production from methane through catalytic partial oxidation reactions," Journal of Power Sources, Elsevier, Amsterdam, NL, vol. 87, No. 1-02, Apr. 1, 2000, pp. 28-38.

* cited by examiner

*Primary Examiner* — Randy Boyer
(74) *Attorney, Agent, or Firm* — Salvatore P. Pace; Iurie A. Schwartz

(57) ABSTRACT

Organic sulfur compounds contained in refinery off gas streams having either high ort low concentrations of olefins are converted to hydrogen sulfides which can be then be removed using conventional amine treating systems. The process uses a catalytic reactor with or without a hydrotreater depending on the olefin concentration of the off gas stream. The catalytic reactor operates in a hydrogenation mode or an oxidation mode to convert a majority of organic sulfur compounds into hydrogen sulfides.

9 Claims, 2 Drawing Sheets

PROCESS FOR SULFUR REMOVAL FROM REFINERY OFF GAS

RELATED APPLICATION

This application claims the benefit of U.S. Provisional Application No. 61/246,592, filed on Sep. 29, 2009, the entire contents of which are incorporated herein by reference in its entirety.

TECHNICAL FIELD

The present invention relates to the removal of sulfur compounds from gases derived from petroleum refinery processes. In one respect, it relates to processes for removing sulfur compounds from refinery off gas streams to create more valuable hydrocarbon containing feed gases, while in another respect it relates to processes to convert organic sulfur compounds to hydrogen sulfides which can be then be removed using conventional amine treating systems.

BACKGROUND

The petroleum refining industry generates large quantities of low value process gases which typically have high concentrations of sulfur compounds. These refinery off gas (ROG) streams, as they are known, are generated from various "secondary" processing technologies used in oil refining such as catalytic cracking, hydro-treating and delayed coking processes. The largest quantity of ROG streams are derived from petroleum cracking units.

ROG streams are comprised of a wide range of gases including hydrogen, carbon monoxide, carbon dioxide and hydrocarbons with more than one carbon atoms including both saturated (paraffins) and unsaturated (olefins) hydrocarbons, such as ethane and ethylene respectively. The content of ethane and ethylene can be as high as 30% and the content of hydrogen is typically in the range of 15 to 50%. The sulfur compounds are typically hydrogen sulfide ($H_2S$), carbonyl sulfide (COS) and organic sulfur compounds such as mercaptans, thiophenes and sulfides. The concentration of $H_2S$ can be greater than 1% by volume and the concentration of organic sulfur compounds can be several hundred parts per million.

Due to the lack of effective technologies for converting ROG streams into more valuable products or useful feed streams, many of these gas streams are used for their fuel value or, in many cases, simply flared. However, even the simple combustion of ROG streams containing high concentrations of sulfur compounds can result in the emission of toxic or other environmentally undesirable gases such as sulfur oxide compounds. Stringent environmental regulations for the emission of these undesirable compounds require that refineries invest in expensive scrubbing systems for more complete sulfur removal from ROG streams prior to or after combustion.

The conversion of high sulfur ROG streams into more valuable low sulfur, hydrocarbon/hydrogen containing streams can reduce energy losses, provide valuable feed streams for further processing, and eliminate many of the environmental concerns associated with the combustion of high sulfur ROG streams. Moreover, since many hydrocarbon conversion processes are catalytic using expensive metal catalysts, the sulfur concentration must be lowered to avoid poisoning the metal catalysts in order to effectively use the hydrocarbon/hydrogen content in the ROG streams as feed gases.

Generally, ROG streams are taken from multiple refinery processing units, collected and desulfurized at a central location in the refinery. However, ROG streams may be required to be taken from a single refinery process and treated and/or used without mixing with other off gas streams due to its specific gas composition.

Many refineries already use amine sulfur removal technology. Amine sulfur removal technology is well known and refers to a group of processes that use aqueous solutions of various amine compounds (commonly referred to simply as amines) to remove $H_2S$ and carbon dioxide ($CO_2$) from sulfur containing gases. While these amine systems are very effective at removing $H_2S$, they are less effective in removing organic sulfur species such as mercaptans, thiophenes, sulfides, and other complex sulfur compounds. For the removal of these organic sulfur compounds, the use of caustic removal systems is generally needed. Caustic removal systems are expensive, use caustic reagents such as potassium hydroxides, which are considered toxic, become consumed and require safe environmental disposal.

Another desulfurization option for fuel gas streams containing organic sulfur compounds is a two-step process consisting of hydrodesulfurization, e.g. the conversion of organic sulfur compounds to $H_2S$, and the subsequent removal of the $H_2S$ with an amine based system or a solid sulfur adsorbent such as ZnO. This approach is typically used for the desulfurization of natural gas feedstocks and ROG streams having low sulfur levels (e.g. 5-10 ppm) such as when natural gas is used as a feedstock in a steam methane reformer for the production of hydrogen. Conventional hydrotreaters in steam methane reformer based hydrogen plants operate at about 300° C.-400° C. utilizing waste heat from the steam methane reforming plant to preheat the feed to the hydrotreater. The catalyst used in conventional hydrotreaters is typically a CoMo or NiMo catalyst.

As mentioned above, the organic sulfur compounds in the ROG streams can be first hydrogenated in a hydrotreating process to form $H_2S$ and then subsequently removed with conventional amine sulfur removal systems. However, for efficient hydrotreating of organic sulfur compounds, heat must be supplied and removed both economically and reliably for the system to convert organic sulfur to $H_2S$. Since the ROG streams are typically received at low pressures, such as 5-10 bar, the hydrotreater must be operated at elevated temperatures in the range of 290°-370° C. to ensure complete conversion of the organic sulfur species. Controlling the temperature within the hydrotreater becomes a key to finding a cost effective sulfur removal process because waste heat is not always available.

Achieving the high temperature needed for hydrogenation of organic sulfur compounds without using an external heat source can be a problem. Hydrogenation of gas streams containing olefins is an exothermic reaction thereby providing heat to the reaction. If the ROG stream does not contain sufficient concentration of olefins, the hydrogenation system will not be able to maintain the proper temperature for conversion of the organic sulfur compounds to $H_2S$ and external heat must be provided to the reactor. If the ROG stream contains too high of a concentration of olefins, the hydrotreating unit can overheat causing the catalyst to be damaged or destroyed.

One solution to this problem is to dilute the high olefin containing ROG stream with a recycle stream from the hydrotreater product. This however requires a recycle compressor which complicates the system, makes it less reliable and increases the cost. Also, ROG streams usually have significant composition variability which makes a hydrotreater with recycle compressor based system difficult to design and control. Last, due to the typical low pressure of ROG feed streams, the hydrotreater operates at low space velocities, such as less than 1000 hr$^{-1}$, which require that the reactors be extremely large adding additional capital costs. Space velocity is defined here as the volumetric flow of ROG streams at standard conditions (standard m$^3$/hr) divided by the reactor volume (m$^3$). Since the cost of the catalytic reactor catalyst is significantly higher than the cost of the conventional hydrotreater catalyst, the better solution could be a combination of the two reactors depending on the management of operating factors such as catalyst cost, pressure and olefin concentration.

Thus the present invention provides a sulfur processing system that is flexible enough to process ROG streams having varying sulfur concentrations, varying organic sulfur compounds, and varying olefin content while still being economical. This invention uses no continuously supplied external heat source for the hydrogenation reaction, eliminates the need to use recycle streams to the hydrotreater to control temperature, and allows for the use of smaller reactors reducing capital costs. Last, the present invention allows for the elimination of a caustic sulfur removal systems and replaces them with a process employing a catalytic reactor used with an amine absorber that is more reliable, easier to operate and can be integrated with the existing refinery amine system.

SUMMARY OF THE INVENTION

The present invention provides a process for removing sulfur compounds from refinery off gas streams to create more valuable hydrocarbon containing feed gases. This invention provides flexibility of operation to address; (a) when the ROG stream contains such low concentrations of olefins that the reaction in the hydrotreater cannot be maintained at temperatures sufficient to convert organic sulfur compounds to H$_2$S without externally supplied heat, and (b) when the ROG stream contains such high concentrations of olefins that the temperature in the conventional hydrotreater becomes too high and damages the catalyst or (c) when the olefin composition variability is such that at any given time the ROG stream will fall into either the (a) or (b) category above or (d) when the ROG steam contains olefin concentrations that can be processed in a conventional hydrotreater but the cost of the reactor/catalyst needed for the catalytic reactor is lower than the conventional hydrotreater reactor.

According to one embodiment of this invention, a process for the removal of sulfur compounds comprising hydrogen sulfide (H$_2$S) and organic sulfur compounds from a refinery off gas feed stream containing hydrogen and a low concentration of olefins is provided, the process comprising:

a) removing at least a portion of the H$_2$S from the feed stream by passing the feed stream through an amine absorber to produce a H$_{2S}$ depleted stream;

b) feeding a first portion of the H$_2$S depleted stream into a catalytic reactor with the addition of oxygen to produce a hot effluent stream exiting the catalytic reactor at a temperature of between about 340° C. and 450° C.;

c) feeding a second portion of the H$_2$S depleted stream into the hot effluent stream exiting the catalytic reactor to form a preheated combined stream, wherein the first portion and second portion are mixed in quantities such that the combined stream is fed into a hydrotreater to maintain the temperature of the hydrotreater to between about 340° C. and 450° C. at the pressure employed;

d) converting a majority of the organic sulfur compounds to hydrogen sulfide in the hydrotreater;

e) cooling the product gas stream exiting the hydrotreater; and f) feeding the cooled product gas stream to an amine sulfur removal system to remove the H$_2$S and produce a hydrocarbon product stream.

In another embodiment of this invention, a process is provided for the removal of organic sulfur compounds from multiple refinery off gas streams containing at least olefins and sulfur compounds including H$_2$S and organic sulfur compounds, wherein a first off gas feed stream contains a high concentration of olefins and a second off gas feed stream contains a low concentration of olefins, the process comprising:

a) feeding the first feed stream to an amine absorber to remove at least part of the H$_2$S to produce a first H$_2$S depleted stream; b) feeding the second feed stream to an amine absorber to remove at least part of the H$_2$S to produce a second H$_2$S depleted stream c) splitting the first H$_2$S depleted stream into a first split stream and a second split stream;

d) feeding the first split stream into a catalytic reactor at a temperature of between 340° C. and 450° C. to convert a majority of the organic sulfur compounds to H$_2$S at the pressure employed and removing a hot first organic sulfur depleted stream from the catalytic reactor;

e) combining the second split stream and second H$_2$S depleted stream are mixed in quantities such that the resulting combined stream is fed into a hydrotreater and maintains the temperature of the hydrotreater to between about 340° C. and 450° C. at the pressure employed and converting the organic sulfur compounds into H$_2$S;

f) removing a second organic sulfur depleted stream from the hydrotreater;

g) combining the first organic sulfur depleted stream and the second organic sulfur depleted stream to form a combined organic sulfur depleted stream;

h) cooling the combined organic sulfur depleted stream; and i) feeding the cooled combined organic sulfur depleted stream to an amine sulfur removal system to remove the H$_2$S and produce a product gas stream.

In yet another embodiment, a process is provided for the removal of H$_2$S and organic sulfur compounds from a refinery off gas feed stream containing at least hydrogen, and a high concentration of olefins comprising:

a) removing at least a portion of the H$_2$S from the feed stream by passing the feed stream through an amine absorber to produce a H$_2$S depleted stream;

b) feeding the H$_2$S depleted stream into a catalytic reactor at a temperature between 340° C. and 450° C. to convert a majority of the organic sulfur compounds to H$_2$S at the pressure employed;

c) cooling the product gas stream exiting the catalytic reactor; and d) feeding the cooled product gas stream to an amine sulfur removal system to remove the H$_2$S and produce a product gas stream.

In yet another embodiment, a process is provided for the removal of H$_2$S and organic sulfur compounds from a refinery off gas feed stream containing hydrogen, carbon oxides and olefins comprising:

a) removing at least a portion of the H$_2$S from the feed stream by passing the feed stream through an amine absorber to produce a H$_2$S depleted stream;

b) determining the olefin concentration of the feed stream or H$_2$S depleted stream;

c) determining the process flow based on the concentration of olefins in the feed stream or the $H_2S$ depleted stream such that;

(I) when the olefin concentration is determined to be 3% or less,
  (i) feeding a first portion of the $H_2S$ depleted stream with the addition of oxygen into a catalytic reactor to maintain the temperature of the catalytic reaction between 340° C. and 450° C. at the pressures employed and convert a majority of the organic sulfur compounds to $H_2S$;
  (ii) feeding a second portion of the $H_2S$ depleted stream into a hot effluent stream exiting the catalytic reactor;
  (iii) feeding the hot effluent stream into a hydrotreater and maintaining a temperature of between 340° C. and 450° C. to convert a majority of the organic sulfur compounds to $H_{2S}$ and produce an $H_{2S}$ rich product gas stream;
  (iv) cooling the $H_2S$ rich product gas stream exiting the hydrotreater; and
  (v) feeding the cooled $H_2S$ rich product gas stream to an amine sulfur removal system to remove the $H_2S$ and produce a sulfur depleted product stream; or (II) when the olefin concentration is determined to be 5% or greater,
  (i) feeding the $H_2S$ depleted stream into a catalytic reactor and maintaining the temperature to between about 340° C. and 450° C. to convert a majority of the organic sulfur compounds to $H_2S$ at the pressures employed and produce a product gas stream; (ii) directing the product gas stream to bypass the hydrotreater, (iii) cooling the product gas stream; and (iv) feeding the cooled product gas stream to an amine sulfur removal system to remove the $H_2S$ to produce a sulfur depleted product stream.

In a final embodiment, a process is provided for the removal of $H_2S$ and organic sulfur compounds from a refinery off gas feed stream containing at least hydrogen, and a low concentration of olefins wherein the hydrogen to olefin molar ratio is greater than 0.5, comprising:

a) removing at least a portion of the $H_2S$ from the feed stream by passing the feed stream through an amine absorber to produce a $H_2S$ depleted stream;

b) feeding the $H_2S$ depleted stream into a catalytic reactor at a temperature between 340° C. and 450° C. to convert a majority of the organic sulfur compounds to $H_2S$ at the pressure employed;

c) cooling the product gas stream exiting the catalytic reactor; and d) feeding the cooled product gas stream to an amine sulfur removal system to remove the $H_2S$ and produce a product gas stream.

BRIEF DESCRIPTION OF THE DRAWINGS

For a more complete understanding of the present invention and the advantages thereof, reference should be made to the following Detailed Description taken in conjunction with the accompanying drawings in which.

DETAILED DESCRIPTION OF THE INVENTION

The process and system of the present invention is directed to the flexible and effective use of olefin containing ROG streams. ROG streams come from multiple sources such as from fluidized catalytic cracking (FCC) units, hydrocracking units, and delayed coking units and contain varying types and concentrations of sulfur compounds. These sulfur compounds, including various organic sulfur compounds as described below, must be removed prior to either further processing of the ROG stream or the use of the ROG stream as a fuel gas.

ROG streams coming from various refinery processes can be combined into a single ROG stream or can be segregated between those containing high olefin concentrations and those containing low olefin concentrations. In most refineries, the ROG streams will naturally have high or low olefin concentrations based on their source. The olefin concentration will determine the optimal sulfur removal process and either a single stream or two streams with varying olefin concentrations can be simultaneously processed. As used herein, ROG streams "having low concentrations of olefins" have olefins concentrations of 3% or less by volume and those "having a high concentrations of olefins" have olefins concentrations of 5% or more by volume. Small variations on these concentrations are possible based on the final composition of the off gas streams as is understood. ROG streams having a middle range of olefins, such as about 4% by volume, can normally be treated with conventional hydrotreating techniques but due to low pressures the space velocity of the conventional hydrotreater can be less than 1000 $hr^{-1}$. In accordance with the present process, sulfur compounds can be effectively removed from all typical ROG streams without significant capital investment or process modification by integration into the existing refinery sulfur removal system and subsequent Claus sulfur removal system. After removal, the sulfur depleted stream can be used as a fuel gas or used as a feed gas stream in further processing. When used as a fuel gas, the refineries can achieve acceptable sulfur oxides emissions.

Figure 1:
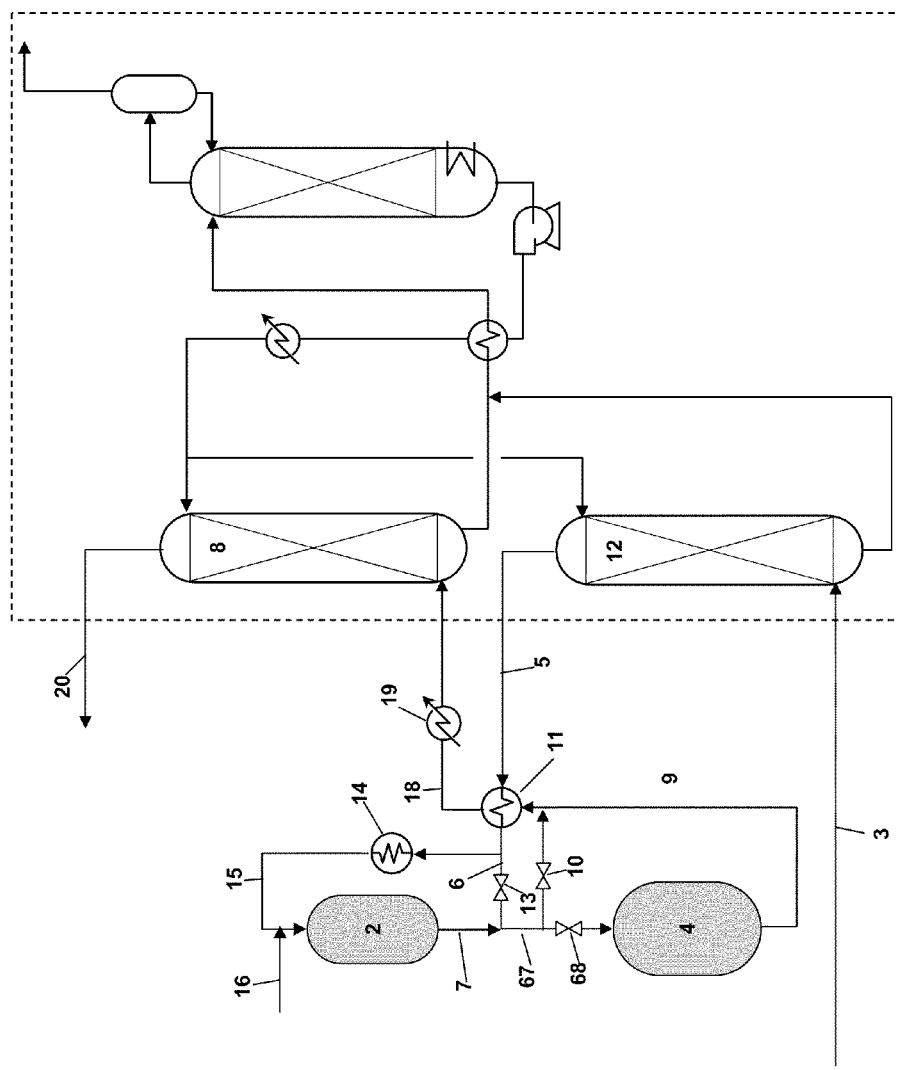
FIG. 1 is a schematic illustrating an embodiment of the invention.

The present process is integrated into conventional sulfur removing systems used in refineries of the type using sulfur absorbers. Such systems are typically amine sulfur removal systems that use aqueous solutions of amines with the most commonly used amines being alkanolamines, monoethanolamine, diethanolamine, and methyldiethanolamine. A typical amine gas treating process includes one or more absorbers, regenerator(s) and accessory process equipment. In the absorber, the down flowing amine solution absorbs $H_2S$ and $CO_2$ from the up flowing sulfur containing gas (sour gas) to produce a sweetened gas stream (i.e., an $H_2S$ depleted stream) as a product gas and an amine solution "rich" in the absorbed acid gases. The resultant rich amine solution is then routed into the regenerator (generally a stripper with a reboiler) to produce regenerated or "lean" amine solution that is recycled for reuse in the absorber. The stripped overhead gas product from the regenerator is a concentrated $H_2S$ and $CO_2$ stream. This $H_2S$-rich stripped gas stream is typically routed into a conventional Claus sulfur removal process to convert the $H_2S$ it into elemental sulfur. In some plants, more than one amine absorber unit may share a common regenerator unit. The amine treating system is shown in FIG. 1 within the doted box and is not individually considered part of this invention.

As used herein, the term "organic sulfur compounds" is intended to include simple, complex and cyclic organic sulfur molecules and species wherein a central sulfur atom is directly attached to one or more carbon atoms. Examples of such compounds include but are not limited to, organosulfur acids, (such as sulfonic, sulfinic and sulfenic acids) and non-acid organic sulfur compounds (such as sulfides, sulfoxides, and sulfones). Many of the sulfur compounds typically found in refinery process gases are know by more common nomenclature such as sulfides, sulfites, thiosulfites, thiophines, mercaptans, disulfides and dialkyl sulfides. It is these organic sulfur compounds that make conventional sulfur removal processes less effective.

According to this invention, ROG streams are treated by the appropriate combination and use of a catalytic reactor and a conventional hydrotreating reactor to convert the organic sulfur compounds within the streams into $H_2S$. The catalytic reactor used in this invention is disclosed in U.S. Pat. Nos. 7,547,422 and 7,037,485 and offers dual mode operation (hydrogenation and oxidation) using the same catalyst and efficient heat integration. The teachings of U.S. Pat. Nos. 7,547,422 and 7,037,485 are incorporated herein by reference. The catalytic reactor that operates at space velocities of greater than 10,000 $hr^{-1}$, preferably greater than 50,000 $hr^{-1}$, and can be used with or without a conventional hydrotreating unit to convert the organic sulfur compounds to $H_2S$. The catalytic reactor used herein can operate in a dual mode either in hydrogenation mode without oxygen or in oxidation mode with oxygen.

The catalytic reactor employs known catalysts that contain one or more group VIII metal, preferably platinum, rhodium, palladium, nickel or ruthenium. The structure of the catalyst is preferably a monolith made of reticulated foam, honeycomb or a corrugated foil wound in spiral configuration although other structures can be employed. Catalyst coated beads, pellets, or ceramic monoliths in the form of reticulated foam or honeycomb structure can also be used.

Generally, the ROG feed stream containing hydrogen is first heated to between about 150-250° C. and then fed into a communicating system of a catalytic reactor and a conventional hydrotreating reactor. When the ROG feed stream has a low concentration of olefins, the heat generated by the conversion reaction of olefins to paraffins in a conventional hydrotreater is not sufficient to maintain reactor temperature at the required range of about 340-400° C. In order to generate the required heat, part of the ROG feed stream can be directed into the catalytic reactor where oxygen, and optionally steam, is added. The heat needed for the reaction is generated in the catalytic reactor by the hydrogen combustion with oxygen. The hot reactant gas exiting the catalytic reactor can then be added to the remaining ROG feed stream and fed to the hydrotreater at the higher temperature so the temperature rise in the hydrotreater (due to conversion of olefins) raises the temperature at the exit of the hydrotreater to the desired range of about 340°-400° C. The ROG feed stream will typically contain hydrogen well in excess of the amount required for the olefin hydrogenation, sulfur conversion and oxygen combustion reactions, but if insufficient hydrogen is present for completion of these reactions, hydrogen can be added as required. In such situations, hydrogen can be added from another hydrogen containing stream, from the existing on site hydrogen production if available, or from storage. The organic sulfur compounds are converted into $H_2S$ at these hydrotreater temperatures. The effluent stream (or product gas) from the hydrotreater is cooled to near-ambient temperature and fed to a conventional amine sulfur recovery unit for $H_2S$ removal.

If the ROG feed stream contains a high concentration of olefins, it can be fed directly to the catalytic reactor which can operate in either hydrogenation mode (no oxygen) or dual mode (with oxygen) as needed. If the hydrotreater is operated at overly high temperatures such as may be generated by the conversion of high concentrations of olefins, the heat sensitive hydrotreating catalyst will be damaged or destroyed. Thus, in this case, the hydrotreater is bypassed. The operation mode of the catalytic reactor, hydrogenation or oxidation, will depend on the pressure of the ROG feed stream and the organic sulfur concentration. The hydrogenation of olefins is favored at higher pressures and lower sulfur concentrations. If the stream condition is such that the extent of olefin hydrogenation does not generate sufficient heat to achieve at least about 340° C. at the reactor exit, oxygen may be added to combust with hydrogen and supply additional heat to meet the temperature requirements. The oxygen addition is controlled so that the reactor exit temperature is maintained at about 340° C.-400° C. Hydrogen is present in excess to ensure that the oxygen conversion is substantially complete. Hydrogen is preferably present in the ROG feed stream in a hydrogen to olefin molar ratio of greater than 0.5 and, more preferably, greater than 1. Generally, if the pressure of ROG feed stream is greater than 10 bar, and more preferably greater than 15 bar, the catalytic reactor will operate in hydrogenation mode. If the pressure of ROG feed stream is less than 10 bar, the catalytic reactor will operate with some oxygen addition. The oxygen addition is used to provide supplemental heat by reaction of oxygen with hydrogen. The amount of oxygen added will depend on the extent of the hydrogenation reaction desired and will be controlled such that the reactor exit temperature is maintained between about 340° C.-450° C. The majority of organic sulfur compounds in the ROG feed stream are converted into $H_2S$ in either mode of operation thereby efficiently using the heat energy of the feed and reducing the risk of catalyst damage. The effluent stream leaving the catalytic reactor is again cooled to near ambient temperature and is fed to a conventional amine sulfur recovery unit for $H_2S$ removal as described above.

Figure 2:
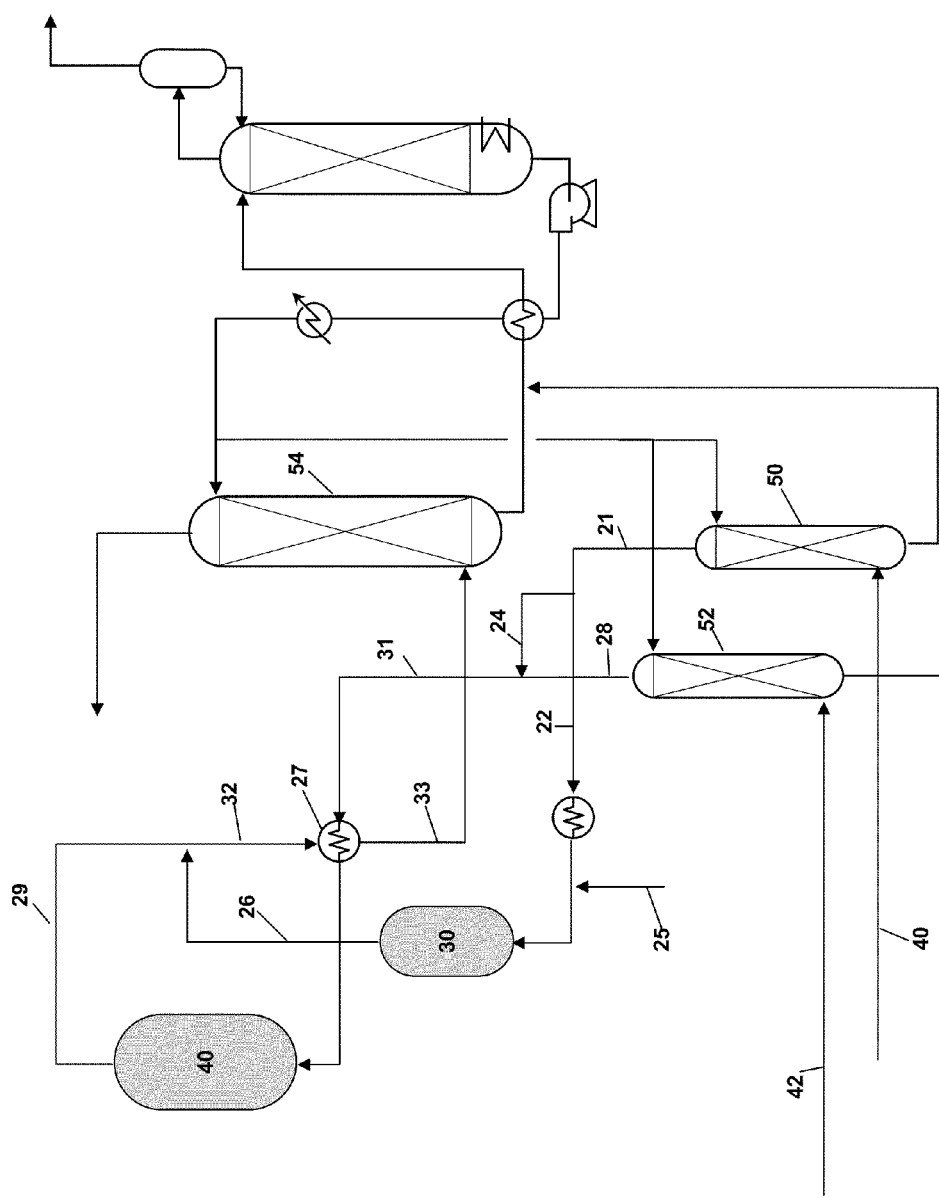
FIG. 2 is a schematic illustrating another embodiment of the invention.

The process of this invention is best understood by reference to the Figures. FIGS. 1-2 illustrate the basic process flow of two embodiments of the present invention. While all essential aspects of the process are shown, additional nonessential aspects or features may be present as is understood and readily apparent to one skilled in the art. The details of the conventional amine treating system are not described since they are well known to one skilled in the art.

Now referring to FIG. 1, a sulfur removal process of one embodiment of this invention is described for situations where there is a single olefin containing ROG feed stream. In this embodiment, the ROG stream can either come directly from one of the refining processes or can be collected from multiple processes and fed as a collected stream. When organic sulfur compounds such as mercaptans, thiophenes and disulfides, are present in combination with $H_2S$, the ROG feed stream (3) is fed to absorber (12) of the amine sulfur removal system (hereinafter "amine treater") which reduces the $H_2S$ concentration to less than about 50 ppm, preferably less than 30 ppm, in the exiting $H_2S$ depleted stream (5). The absorber (12) may already be associated with or integrated into the amine treater, but will typically be a separate unit added for proposes of conducting the inventive process. Since most organic sulfur compounds cannot be substantially removed in the amine treater and may remain in amounts of greater than 50 ppm (and in amounts as high as several hundred ppm), additional processing is required.

The $H_2S$ depleted stream (5) leaving absorber (12) and continuing to having high concentrations of organic sulfur compounds is first preheated in recuperator (11) or other suitable heat exchanger, and then split into two streams shown as streams (15 and 6). First split stream (15) is sent to the catalytic reactor (2) and second split stream (6) is sent to the hydrotreater (4). A sufficient amount of oxygen is introduced into first split stream (15) through line (16) before passing into the catalytic reactor (2) to operate the reactor in the oxidation mode and to provide the needed heat for the conversion reaction. Optionally, first split stream (15) may be preheated in a conventional start-up heater (14) to be heated during start up. The flow of oxygen through line (16) and first split stream (15) are adjusted to provide sufficient reaction with the hydrogen present in ROG feed stream (3) to produce water and heat to raise the temperature within catalytic reactor (2) and of the effluent stream (7) leaving catalytic reactor (2) to between about 340° C.-450° C. By maintaining the reaction temperature of the effluent stream (7) above about 340° C., the majority of the organic sulfur compounds, typically more than 60%, and preferably greater than 70%, are converted to $H_2S$.

The effluent stream (7) exiting the catalytic reactor (2) is then mixed with the second split stream (6) and is fed through line (67) to hydrotreater (4). The mixing of the hot effluent stream (7) exiting the catalytic reactor (2) and the cooler second split stream (6) results in a preheated combined stream (67) with sufficiently high temperature so that the hydrotreater (4) can convert the organic sulfur compounds to $H_2S$, even with the low concentration of olefin present. The temperature of the combined stream (67) is controlled to be between 200° C. and 350° C., more preferably between 225° C. and 275° C. by the volume of gas from second split stream (6) added to effluent stream (7). Depending on the olefin concentration of ROG feed stream (3), the volume of gas from first split stream (15), the volume of gas from second split stream (6), and the volume of oxygen added to first split stream (15) can be adjusted to maintain the desired temperature range at the hydrotreater (4) entrance. This can be determined by one skilled in the art by monitoring the temperatures of the various steams or can be automated using processors and value actuation means. The hydrotreated effluent stream (9) exits the hydrotreater (4) at about 340-400° C., is cooled by heat exchange with the $H_2S$ depleted stream (5) through recuperator (11), is sent through line (18) to cooler (19) and to absorber (8) of the amine treater to remove $H_2S$. The hydrocarbon product stream (20) will have a low level of sulfur remaining, preferably below 20 ppm of sulfur compounds. Absorber (8) is typically already present in the existing amine treater. Further processing can be done to this stream if desired to remove sulfur with a solid sulfur adsorbent such as zinc oxide, iron oxide, activated carbon or caustic treatment or any other polishing sulfur removal technique to further reduce sulfur levels using conventional systems.

Again referring to FIG. 1, an alternative operation is shown for situations in which the ROG feed stream contains a high concentration of olefins and is provided to the sulfur removing process at either high or low pressures. For the purpose of this invention, high pressures are 10 bar or greater and low pressures are less than 10 bar. In this embodiment, the hydrotreater (4) can be bypassed by closing valves (13) and (68) and opening valve (10). In this manner, the olefin containing ROG feed stream (3) can be processed without the conventional hydrotreater (4) with the effluent stream (7) exiting the catalytic reactor (2) and bypassing hydrotreater (4) through bypass value (10) as shown. This embodiment is shown in a bypass mode with bypass valves present for ease of explanation, but can be employed as a stand alone sulfur removal system wherein hydrotreater (4) and bypass values (13, 68, and 10) are excluded from the process.

The ROG feed stream (3) containing a high olefin concentration as well as a high $H_{2S}$ content is provided to absorber (12) at a low pressure, such as less than 10 bar, and treated by absorber (12) to reduce the $H_2S$ content, preferably to less than 20 ppm. The $H_2S$ depleted stream (5), leaves adsorber (12) with a high olefin content, and passes into catalytic reactor (2) through line (15) which is not split (valve 13 being closed) and where it is mixed with oxygen sent from line (16).

Optionally $H_2S$ depleted stream (5) can be preheated by heater (14) as described above. The oxygen from line (16) will react with the hydrogen present to produce water and heat thereby raising the temperature of the effluent stream (7) exiting catalytic reactor (2) to between 250° C. and 450° C., preferably between 300° C. and 400° C. Alternatively, when the pressure of the RGP stream (3) is high, 10 bar or higher and preferably above 15 bar, the catalytic reactor (2) can operate solely in hydrogenation mode with no oxygen addition (the oxygen flow being stopped in such situation). The required heat will be provided in this situation by the hydrogenation of olefins contained in stream (15). The majority of the organic sulfur compounds in the ROG feed stream (3), more than 60% and preferably 70%, will convert to $H_{2S}$ from either the oxidation and/or hydrogenation reactions provided that the temperature of the effluent stream (7) remains above 300° C. The effluent stream (7) bypasses the hydrotreater (4) through bypass valve (10), is cooled by preheating with $H_{2S}$ depleted stream (5) exiting adsorber (12) through recuperator (11) and sent through line (18) to cooler (19) to bring the gas stream to near ambient temperature before being sent to absorber (8) of the amine treater. Again, the amine treater (8) removes $H_{2S}$ to low levels, such as below 20 ppm of sulfur compounds.

In another embodiment of this invention, two ROG streams are processed for the removal of sulfur. These ROG feed streams are either already received separately in the refinery or can be segregated into two ROG feed streams. One of the streams will contain high concentrations of olefins (5% or greater by volume) and one stream will contain low concentrations of olefins (3% or less by volume).

Referring now to FIG. 2, a first ROG feed stream containing a high olefin concentration (40) is sent through amine absorber (50), exits as a first $H_2S$ depleted stream (21) and is split into a first split stream (24) and a second split stream (22). A second ROG feed stream containing a low olefin concentration (42) is sent through amine absorber (52) and exits as a second $H_2S$ depleted stream (28). Second $H_2S$ depleted stream (28) joins first split stream (24) to form first combined stream (31) which is sent through recuperator (27) and to the hydrotreater (40). Hydrotreater (40) converts the organic sulfur compounds within the first combined stream (31) to $H_2S$ and hydrogenates the olefins contained within first combined stream (31) to provide the heat required for the conversion reaction. The second split stream (22) is optionally mixed with oxygen fed through line (25) and sent to the catalytic reactor (30) to convert organic sulfur compounds to $H_2S$. If the pressure and sulfur concentration of second split stream (22) is such that the olefins hydrogenate to raise the reactor temperature to above about 340° C., no oxygen is added and the oxygen flow is stopped. If the hydrogenation reactions are not sufficient to raise the temperature above about 340° C., then oxygen is added which will react with the hydrogen present to produce additional heat to raise the temperature to about 340-400° C. Generally, above 10 bar or greater and preferably above 15 bar, catalytic reactor (30) can operate in the hydrogenation mode with no oxygen addition and no oxygen is introduced into second split stream (22). In this case, the required heat to sustain the reaction is provided by the hydrogenation of olefins.

The organic sulfur depleted gas exiting catalytic reactor (30) and hydrotreater (40) exiting through lines (26) and (29), respectively, are combined to form a second combined stream (32) and cooled by preheating with a second $H_2S$ depleted ROG feed stream (31) through recuperator (27). The cooled product stream (33) is sent to the amine treater (54) for $H_2S$ removal to provide a hydrocarbon stream with low sulfur concentration, such as below 20 ppm. By varying the mixing volumes and flow ratio of the first split stream (24) having a high olefin concentration and the second $H_2S$ depleted ROG feed stream (28) having a low olefin concentration, the appropriate concentration of olefins in the first combined stream (31) can be sent to hydrotreater (40) to maintain the temperature at the desired window of operation, from about 340° C.-450° C. Determining the mixing volumes is easily done by one skilled in the art after measuring the olefin concentration of the ROG feed streams and considering the process and temperature requirements.

Other variations of the present invention include the use of alternative sulfur removal systems in place of the amine treater. Although the invention has been described in detail with reference to certain embodiments, those skilled in the art will recognize that there are other embodiments of the invention within the spirit and the scope of the claims.

What is claimed is:

1. A process for the removal of sulfur compounds comprising hydrogen sulfide ($H_2S$) and organic sulfur compounds from a refinery off gas feed stream containing hydrogen and a low concentration of olefins, the process comprising:
   a) removing at least a portion of the $H_2S$ from the feed stream by passing the feed stream through an amine absorber to produce a $H_2S$ depleted stream;
   b) feeding a first portion of the $H_2S$ depleted stream into a catalytic reactor with the addition of oxygen to produce a hot effluent stream exiting the catalytic reactor at a temperature of between about 340° C. and 450° C.;
   c) feeding a second portion of the $H_2S$ depleted stream into the hot effluent stream exiting the catalytic reactor to form a preheated combined stream, wherein the first portion and second portion are mixed in quantities such that the combined stream is fed into a hydrotreater to maintain the temperature of the hydrotreater to between about 340° C. and 450° C. at the pressure employed;
   d) converting a majority of the organic sulfur compounds to hydrogen sulfide in the hydrotreater;
   e) cooling the product gas stream exiting the hydrotreater; and
   f) feeding the cooled product gas stream to an amine sulfur removal system to remove the $H_2S$ and produce a hydrocarbon product stream.

2. The process of claim 1 wherein the refinery off gas feed stream has a concentration of olefins of about 3% or less.

3. The process of claim 1 wherein more than 60% of the organic sulfur compounds are converted to $H_2S$.

4. The process of claim 1 wherein hydrogen is present in a hydrogen to olefin molar ratio of greater than 1.

5. The process of claim 1 wherein the hydrocarbon product stream has below 20 ppm sulfur compounds.

6. The process of claim 1 wherein a first portion of the $H_2S$ depleted stream is preheated by a conventional start-up heater.

7. The process of claim 1 wherein the catalytic reactor is a dual mode reactor capable of operating in a hydrogenation mode or an oxidation mode at space velocities of greater than 10,000 $hr^{-1}$.

8. The process of claim 7 wherein the catalytic reactor operates at space velocities of greater than 50,000 $hr^{-1}$.

9. The process of claim 1 wherein the product gas stream exiting the hydrotreater is cooled by to near ambient temperature by heat exchange with the $H_2S$ depleted stream through a heat exchanger.

* * * * *